(12) United States Patent
Westerink et al.

(10) Patent No.: US 11,690,546 B2
(45) Date of Patent: Jul. 4, 2023

(54) DEVICE, SYSTEM AND METHOD FOR DETERMINING AN EMOTIONAL STATE OF A USER

(71) Applicant: KONINKLIJKE PHILIPS N.V., Eindhoven (NL)

(72) Inventors: Joanne Henriette Desiree Westerink, Eindhoven (NL); Martin Ouwerkerk, Culemborg (NL)

(73) Assignee: Koninklijke Philips N.V., Eindhoven (NL)

( * ) Notice: Subject to any disclaimer, the term of this patent is extended or adjusted under 35 U.S.C. 154(b) by 579 days.

(21) Appl. No.: 16/610,953

(22) PCT Filed: May 29, 2018

(86) PCT No.: PCT/EP2018/064098
§ 371 (c)(1),
(2) Date: Nov. 5, 2019

(87) PCT Pub. No.: WO2018/219965
PCT Pub. Date: Dec. 26, 2018

(65) Prior Publication Data
US 2020/0100718 A1    Apr. 2, 2020

(30) Foreign Application Priority Data
May 30, 2017   (EP) .................................... 17173491

(51) Int. Cl.
*A61B 5/16* (2006.01)
*A61B 5/053* (2021.01)
(Continued)

(52) U.S. Cl.
CPC ............ *A61B 5/165* (2013.01); *A61B 5/0533* (2013.01); *A61B 5/681* (2013.01); *A61B 5/7275* (2013.01);
(Continued)

(58) Field of Classification Search
None
See application file for complete search history.

(56) References Cited

U.S. PATENT DOCUMENTS 8,622,900 B2   1/2014  Jain
10,085,695 B2  10/2018 Ouwerkerk
(Continued)

FOREIGN PATENT DOCUMENTS

JP    2017042262 A   3/2017

OTHER PUBLICATIONS

Van Dooren, M., de Vries, J. J., & Janssen, J. H. (2012). Emotional sweating across the body: comparing 16 different skin conductance measurement locations. Physiology & Behavior, 106(2), 298-304.
(Continued)

*Primary Examiner* — Benjamin S Melhus

(57) ABSTRACT

The present invention relates to a device, system and method for determining an emotional state of a user based on emotion-induced cortisol estimation. The device comprises an interface (11) for obtaining a psychophysiological signal trace (22) indicative of one or more measured stimulus responses corresponding to a neural stress response; a processing unit (12) for processing the psychophysiological signal trace, wherein the processing unit is configured to determine one or more stimulus responses (29) in the psychophysiological signal trace (22); to determine a first contribution (91) to an estimated future cortisol level trace (93) based on the one or more determined stimulus responses (29) in the psychophysiological signal trace (22); to determine a second contribution (92) to the estimated future cortisol level trace (93) based on one or more anticipated future stimulus responses (96); and to determine an estimated future emotional state of the user based on said first and said second contribution to the estimated future cortisol level trace (93). The invention further relates to a corresponding computer program and a wearable device (30).

19 Claims, 8 Drawing Sheets

(51) Int. Cl.
*A61B 5/00* (2006.01)
*G16H 50/30* (2018.01)
*G16H 10/60* (2018.01)
*A61B 5/0533* (2021.01)

(52) U.S. Cl.
CPC .......... *A61B 5/7278* (2013.01); *G16H 10/60* (2018.01); *G16H 50/30* (2018.01)

(56) References Cited

U.S. PATENT DOCUMENTS

| | | | |
|---|---|---|---|
| 10,881,345 B2* | 1/2021 | Unni | A61B 5/4884 |
| 11,129,568 B2* | 9/2021 | Olivier | A61B 5/318 |
| 2014/0128764 A1* | 5/2014 | Gandhi | A61B 5/369 |
| | | | 600/544 |
| 2014/0288401 A1 | 9/2014 | Ouwerkerk et al. | |
| 2017/0000398 A1 | 1/2017 | Ouwerkerk et al. | |
| 2017/0127993 A1* | 5/2017 | Olivier | A61B 5/6823 |
| 2018/0146898 A1* | 5/2018 | Begtrup | A61B 5/02405 |
| 2019/0192001 A1* | 6/2019 | Heikenfeld | B05D 3/007 |
| 2020/0163606 A1* | 5/2020 | Kallen | A61B 5/02055 |

OTHER PUBLICATIONS

Cueva, C., Roberts, R. E., Spencer, T., Rani, N., Tempest, M., Tobler, P. N., & Rustichini, A. (2015). Cortisol and testosterone increase financial risk taking and may destabilize markets. Scientific reports, 5, 11206.
International Search Report and Written Opinion from PCT/EP2018/064098 dated Aug. 17, 2018.

* cited by examiner

DEVICE, SYSTEM AND METHOD FOR DETERMINING AN EMOTIONAL STATE OF A USER

CROSS-REFERENCE TO PRIOR APPLICATIONS

This application is the U.S. National Phase application under 35 U.S.C. § 371 of International Application No. PCT/EP2018/064098, filed on May 29, 2018, which claims the benefit of EP Patent Application No. EP 17173491.6, filed on May 30, 2017. These applications are hereby incorporated by reference herein.

FIELD OF THE INVENTION

The present invention relates to a device, system and method for determining an emotional state of a user based on emotion-induced cortisol estimation. Further, the present invention relates to a corresponding computer program for carrying out said method. The present invention further relates to a wearable device wearable by a user and comprising such a system for determining an emotional state of the user based on emotion-induced cortisol estimation.

BACKGROUND OF THE INVENTION

Stress is characterized by a series of bodily responses, including an increased heart rate, increased sweating resulting in a rise in skin conductance, and the release of the stress hormone cortisol with a delay of about 20-30 min. These bodily responses facilitate an adequate response towards an actual or perceived stressor, such as a threat, or a surprise, or any other stimulus or event that causes stress. Too high cortisol levels, however, are counter-productive, since they cause cognitive impairment (Klaassen, E. B., de Groot, R. H., Evers, E. A., Nicolson, N. A., Veltman, D. J., & Jolles, J. (2013). Cortisol and induced cognitive fatigue: effects on memory activation in healthy males. Biological Psychology, 94(1), 167-174) and affect decision making due to increased risk taking behavior.

WO 2013/076615 A1 (corresponding to US 2014/0288401 A1), an earlier patent application of the inventors, discloses a mental balance or imbalance estimation system and method for estimating a level of mental balance or imbalance of a user based on emotion-induced cortisol estimation.

The system disclosed in WO 2013/076615 A1 comprises a skin conductance sensor for sensing the skin conductance of the user, the skin conductance over time forming a skin conductance trace. The system further comprises a processing unit for receiving and processing the skin conductance trace, wherein the processing unit is configured to determine at least one stimulus response in the skin conductance trace, to determine an estimated cortisol level trace of the user based on the determined at least one stimulus response, and to determine the estimated level of mental balance or imbalance of the user based on the estimated cortisol level trace.

The solution described in the WO 2013/076615 A1 provides an advantageous approach, in particular for real-time assessment of a cumulative stress load and can assist a user to reduce the risk of allostatic overload.

SUMMARY OF THE INVENTION

It would be advantageous to provide a further improved device, system and method for determining an emotional state of a user based on emotion-induced cortisol estimation, as well as a wearable device comprising such a system, and a computer program implementing such a method.

In accordance with a first aspect of the present invention a device for determining an emotional state of a user based on emotion-induced cortisol estimation is presented, the device comprising:

an interface for obtaining a psychophysiological signal trace (indicative of one or more measured stimulus responses corresponding to a neural stress response);

a processing unit for processing the psychophysiological signal trace, wherein the processing unit is configured to determine one or more stimulus responses in the psychophysiological signal trace;

determine a first contribution to an estimated future cortisol level trace based on the one or more determined (past) stimulus responses in the (measured past) psychophysiological signal trace;

determine a second contribution to the estimated future cortisol level trace based on one or more anticipated future stimulus responses; and determine an estimated future emotional state of the user based on said first and said second contribution to the estimated future cortisol level trace.

In accordance with a further aspect of the present invention a system for determining an emotional state of a user based on emotion-induced cortisol estimation is presented, the system comprising a sensor for measuring a psychophysiological signal indicative of one or more measured stimulus responses corresponding to a neural stress response of the user; and the afore-mentioned device.

In accordance with another aspect of the present invention a wearable device wearable by a user is presented, the device comprising the afore-mentioned system.

In accordance with yet another aspect of the present invention, a method for determining an emotional state of a user based on emotion-induced cortisol estimation is presented, the method comprising the steps of:

obtaining a psychophysiological signal trace indicative of one or more measured stimulus responses corresponding to a neural stress response;

determining one or more stimulus responses in the psychophysiological signal trace;

determining a first contribution to an estimated future cortisol level trace based on the one or more determined (past) stimulus responses in the (measured past) psychophysiological signal trace;

determining a second contribution to the estimated future cortisol level trace based on one or more anticipated future stimulus responses; and determining an estimated future emotional state of the user based on said first and said second contribution to the estimated future cortisol level trace.

In yet further aspects of the present invention, there are provided a corresponding computer program which comprises program code means for causing a computer to perform the steps of the method disclosed herein, when said computer program is carried out on a computer, as well as a non-transitory computer-readable recording medium that stores therein a computer program product, which, when executed by a processor, causes the method disclosed herein to be performed.

Preferred embodiments of the invention are defined in the dependent claims. It shall be understood that the claimed device, system, wearable device, method, computer program and medium can have similar and/or identical preferred embodiments as the claimed device, in particular as defined in the dependent claims and as disclosed herein. Furthermore, the method and computer program product according to the invention is advantageous for analogous reasons as the corresponding features of the device/ system according to invention.

The present invention is based on the idea to further improve the solution as described in the earlier application of the present inventors (WO 2013/076615 A1 as mentioned above), in that instead of only considering a first contribution to an estimated cortisol level trace of the user based on at least one stimulus response in a past measured skin conductance trace, also a second contribution to the estimated future cortisol level trace is taken into account based on one or more anticipated future stimulus responses.

It has been found that WO 2013/076615 can provide a good estimate for a current cortisol level. Moreover, since the release of the stress hormone cortisol involves a delay of typically 20-30 min to its maximum and a total duration of about 90-150 min, the measurement of one or more stimulus responses in the (measured past) psychophysiological signal trace not only allows an estimation of the current cortisol levels, but also allows an estimation or prediction of the cortisol level that will occur in the very near future (up to about 15 min). This is logical, since a stimulus response such as a skin conductance peak at the current moment is sure to yield a cortisol contribution with a maximum after 20-30 min.

However, the estimation of the cortisol level trace therein is only based on skin conductance measurement that are done in the past up until a current point in time, and it does not take into account what might happen between the current point in time and a potential future moment for which the cortisol prediction is needed. Hence, the cortisol level may be underestimated. The assumption that no additional stress responses will be evoked in the future can be seen as a scenario wherein the user will abruptly change to a stimulus-free environment. The solution proposed herein, however, is based on the assumption that if a person is in a state exposed to stressors, it is reasonable to assume that the exposition to such stressors will not end abruptly but may also continue at least in the near future. Hence, the cortisol level estimation can be further improved in that a second contribution to the estimated future cortisol level trace is taken into account based on one or more anticipated future stimulus responses that can be expected to also lead to an associated contribution to a future cortisol level.

Thereby, the solution according to an aspect of present invention offers a more realistic and accurate estimation of cortisol excretion in the (near) future. As a further advantage, a length of a prediction interval may be extended.

In other words, while the past psychophysiological signal trace allows an estimation of the emotion-induced cortisol at the present moment in time and to a certain extent into the near future, the solution proposed herein can further improve the accuracy of such a prediction by an estimation of the expected frequency and severity of stressors that may occur between now and the moment for which the cortisol prediction is calculated.

Similar to WO 2013/076615 A1, which is incorporated herein by reference in its entirety, the underlying concept is to estimate or model an (emotion- or stress-induced) contribution to a (salivary) cortisol level trace (which is a cortisol level over time) linked to stress based on a measurement of a psychophysiological signal trace e.g. based on skin conductance measurements. It is known that a stimulus (or stressor or emotional event) causes (with a short latency) a stimulus response corresponding to a neural stress response for example in the skin conductance (skin conductance response) which can be measured. It has been found that there is a specific relationship between a stimulus response (e.g. skin conductance response) in the psychophysiological signal trace, e.g. the skin conductance trace, and a (salivary) cortisol time response of a user. Thus, there is a specific relation between the measured stimulus response and a subsequent cortisol response. The cortisol response linked to a stimulus response has in particular specific (time) latency. This latency is in particular much bigger than the latency between the stimulus and its stimulus response. In particular, it has been found that there is a specific latency between the peak in the skin conductance trace and the peak of the corresponding cortisol time response. Also it has been found that the cortisol time responses can be cumulated or added on top of each other.

Correspondingly, the first contribution to an estimated future cortisol level trace based on the one or more past determined stimulus responses in the (measured past) psychophysiological signal trace and the second contribution to the estimated future cortisol level trace based on one or more anticipated future stimulus responses can also be cumulated or added on top of each other.

Using this knowledge, since the (emotion-induced) cortisol level is indicative of an emotional state of the user, the emotional state of the user can be estimated, for example in form of estimating a level of mental balance or imbalance of the user as described in WO 2013/076615 A1.

In particular, a quantification of the cumulative effect of the first contribution of the measured past stimulus responses and the second contribution due to anticipated future stimulus responses in a specific future time frame can be provided. Hence, with the present invention an improved prediction of an altered stress response in the near future can be given taking into account the impact of (severe) stimuli (or stressors) that have been measured in the past and anticipated future stimuli that are expected to occur. If the second contribution is not taken into account, there is a risk that the future cortisol level trace may be underestimated.

In an embodiment the psychophysiological signal trace is a skin conductance signal trace indicative of a skin conductance of the user over time. An advantage of this embodiment is that the skin conductance can be conveniently measured, for example, with a wearable device and has been found to provide a reliable indication of the neural stress response of the user. The skin conductance signal trace can be processed as described in detail in WO 2013/076615 A1 to determine one or more stimulus responses. In addition or in the alternative, measurements of other parameters that are linked to the (fast) neural effects can be evaluated such as heart rate increases, breathing rate increases pupil dilation, heart-rate variability (HRV), piloerector activation, vasodilation, more generally parameters that are linked to sympathetic-adreno-medullary (SAM) pathway in particular such parameters that are linked to (Nor)adrenaline/acetylcholine release that are indicative of and provide stimulus responses corresponding to a neural stress response.

Optionally, the processing unit can be configured to determine said first contribution to the estimated future cortisol level trace in an upcoming second predetermined window based on the one or more determined stimulus responses in the psychophysiological signal trace in a past first predetermined time window; and to determine said second contribution to the estimated future cortisol level trace in the upcoming second predetermined time window based on one or more anticipated future stimulus responses, which are expected to occur in said second predetermined time window. The first time window may immediately precede the current point in time. The second time window may immediately follow the current point in time. Advantageously, the processing unit is configured to determine the one or more anticipated future stimulus responses in the upcoming second predetermined time window based on one or more past stimulus responses in the first predetermined time window. Thereby, the impact of the stimulus responses in the first predetermined time window is essentially considered twice. This is a reasonable assumption provided that the user keeps doing what he has been doing lately.

Optionally, said anticipated future stimulus responses are determined based on the one or more past stimulus responses in the psychophysiological signal trace in said first predetermined time window. For example, the anticipated future stimulus responses may be determined based on the last minutes preceding the current point in time, for example, based on the determined stimulus responses in the last 5, 10, 20 or 30 minutes preceding the current point in time. An improved accuracy can be achieved in that more recent data is considered since an abrupt change is less likely. Optionally, information about past stimulus responses in the psychophysiological signal trace can be used several times for example by replicating the information in the first predetermined time window preceding the current point in time as information following the current point in time. A further advantage of this embodiment is a reduced memory requirement.

Optionally, the one or more stimulus responses in the second time window can be equal to or reversed in order with respect to the one or more stimulus responses in the first time window. Hence, an accurate prediction can be made under the assumption that the user keeps doing what he has been doing. Reversing the order of the anticipated stimulus following the current point in time compared to the order of the measured stimulus responses preceding the current point in time is reasonable since a higher correlation can be expected for information having a similar absolute temporal distance with respect to the current point in time. In other words, the information about the one or more stimulus responses can advantageously be mirrored with respect to the current point in time. For example, an anticipated stimulus response at time +t1, e.g. 5 minutes into the future, can correspond to a determined (measured) stimulus response at time −t1, e.g. 5 minutes into the past; and an anticipated stimulus response at time +t2, e.g. 10 minutes into the future, can correspond to a determined (measured) stimulus response at time −t2, e.g. 10 minutes into the past.

Optionally, determining said second contribution to the estimated future cortisol level trace comprises extrapolating the psychophysiological signal trace to obtain an extrapolated psychophysiological signal trace; determining one or more anticipated future stimulus responses in the extrapolated psychophysiological signal trace; and determining said second contribution to the estimated future cortisol level trace based on said one or more anticipated future stimulus responses. An advantage of this embodiment is that the same signal processing can continuously be applied to past measured and future anticipated signal. If the user continues with a previous activity or exposition to a scenario evoking stimulus responses, a similar psychophysiological signal trace can be expected such that a current measured psychophysiological signal may be extrapolated into the future.

Optionally, the processing unit can be configured to extrapolate the psychophysiological signal trace such that at least a segment of the extrapolated (future) psychophysiological signal trace corresponds to a segment of the (measured past) psychophysiological signal trace. Hence, the signal trace can be used at least twice, i.e. once for the time that was actually measured (in the past) and once as an estimate for a time interval that lies in the future. For example, a signal trace in an upcoming second time window can correspond to a trace a past first time window. This also enables a very memory efficient implementation, since it is not mandatory to store the same segment twice. For example a pointer can point the same memory portion where the segment has been stored, again. Optionally, a segment of the psychophysiological signal trace in the recent past, preferably immediately preceding the current point in time can be repeated to obtain the extrapolated psychophysiological signal.

Optionally, the processing unit can be configured to extrapolate the psychophysiological signal trace such that at least a segment of the extrapolated psychophysiological signal trace corresponds to a segment of the psychophysiological signal trace that is reserved in time. An advantage of this embodiment is that the portion of the extrapolated psychophysiological signal trace following the current point in time is closely related to the portion of the psychophysiological signal trace immediately preceding the current point in time.

Optionally, the processing unit can be configured to determine said second contribution to the estimated future cortisol level trace based on historic data indicative of one or more anticipated future stimulus responses. For example, the second contribution to the estimated future cortisol level trace can be determined based on one or more anticipated future stimulus responses, for example, from a same or similar period of a previous day for example yesterday, last week, same day of the week, on a similar leisure or working day or a day having a similar profile of preceding measured stimulus responses.

Optionally, the processing unit can be configured to determine the one or more anticipated future stimulus responses based on a weighted combination of one or more anticipated future stimulus responses. For example, a weighted average using one or more of the afore-mentioned methods such as replicating segments, mirroring, averaging, and/or using historic data can be used. Correspondingly, besides determining an estimated future emotional state of the user based on said first and said second contribution of the estimated future cortisol level trace, one or more additional contributions to the estimated future cortisol level trace can be taken into account. The estimated future emotional state of the user can then be determined based thereon.

Optionally, the processing unit can be configured to determine a first and a second estimated future emotional state of the user by
(a) determining a first second contribution to the estimated future cortisol level trace based on one or more first anticipated future stimulus responses; and
determining a first estimated future emotional state of the user based on said first and said first second contribution to the estimated future cortisol level trace; and
(b) determining a second second contribution to the estimated future cortisol level trace based on zero or more second anticipated future stimulus responses; and
determining a second estimated future emotional state of the user based on said first contribution to the estimated future cortisol level trace and said second second contribution to the estimated future cortisol level trace. An advantage of this embodiment is that different scenarios can be assessed. For example, the first second contribution to the estimated future cortisol level trace can be determined under the assumption that the user keeps doing what he has been doing lately; whereas the second second contribution to the estimated future cortisol level trace can be determined under the assumption that the user tries to reduce the exposition to stressors. For example the potential effect of taking counter measures to stressors can be indicated, such as guided breathing, starting meditation, providing the user with calming music or a calming lighting situation. Of course it is also possible to make a prediction regarding the estimated future emotional state if the user is exposed to a more intense and/or more stressful situation. Furthermore, different profiles in particular temporal profiles of exposition to anticipated future stimuli and corresponding anticipated future emotional states can be simulated. Optionally, an indication can be provided when the user is expected to enter into a cognitive less preferred state, and how long he is expected to stay there.

Optionally, said second second contribution to the estimated future cortisol level is lower than said first second contribution to the estimated future cortisol level trace. For example, the second estimate can be determined based under the assumption that the user avoids stress from now on.

Optionally, the system can comprise an output unit for outputting the future emotional state to the user. Thereby, the user can be provided with information about his estimated future emotional state. A user as used herein, can also refer to the user of the output unit e.g. a clinician, medical personnel.

Advantageously, the estimated future emotional state of the user not only provides an indication of the momentary emotional state (e.g. a state of mental balance or imbalance) of the user but it can make an estimation of the upcoming future emotional states of the user in different scenarios. For example, the user can be warned about a potential undesirable estimated future emotional state during a following time period (e.g. during the next 30 min) if the user keeps on doing what he has been doing. In particular, the estimation or prediction of the emotional state, for example a level of imbalance in the case of severe emotional events, can extend a specific time period into the future (e.g. 150 min into the future). As such, the device, system or method can guide a user (e.g. a person) to prevent over stressed states that can be harmful to the health of the user. Based on the estimated future emotional state of the user an output can be rendered to the user, for example in the form of an advice not to drive a car for such time period into the future. Moreover, different scenarios can be presented to the user to indicate what exposition to stressors can be tolerated in order to stay within healthy limits.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
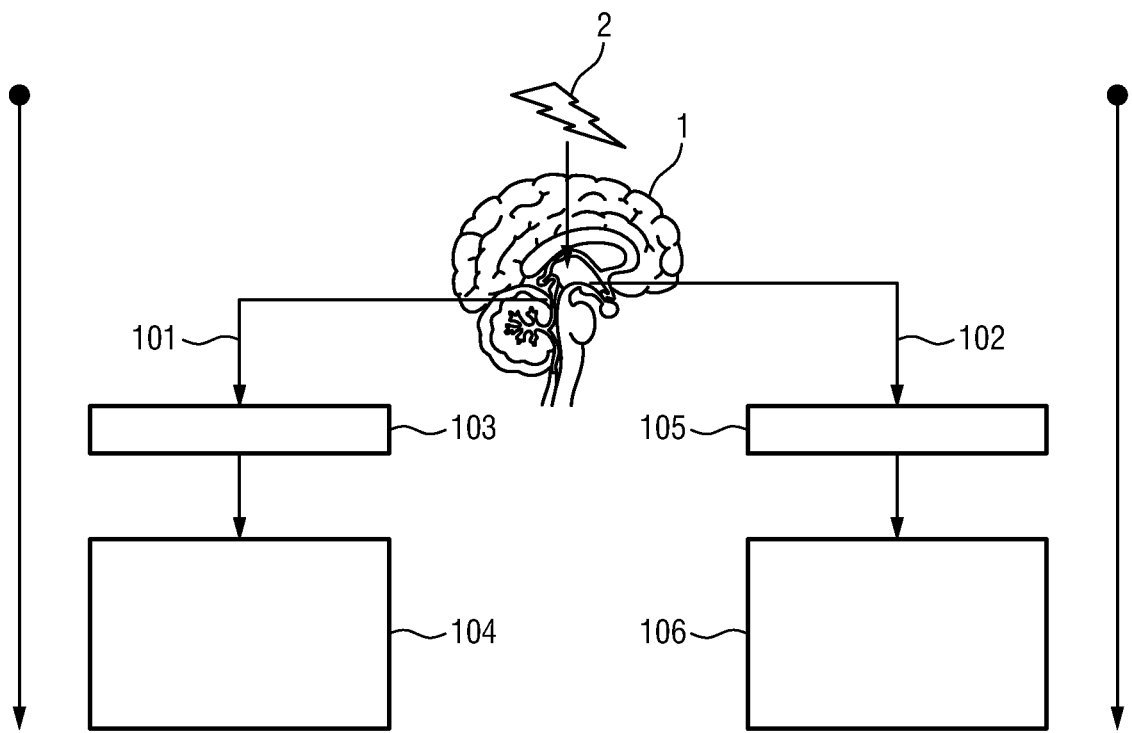
FIG. 1 shows an illustration of the neural and hormonal response paths in response to a stressor.

FIG. 1 shows an illustration of the different neural and hormonal response paths in response to a stressor. When the subject 1 experiences a stressor 2, there are different pathways for the neural and hormonal responses to stress, namely the sympathetic-adreno-medullary (SAM) pathway 101 which provides a fast response, e.g. on the time scale of seconds, and the hypothalamic-pituitary-adrenal (HPA) pathway 102 which provides a slow response, e.g. on the time scale of minutes. The SAM pathway 101 leads to (Nor-) adrenaline/acetylcholine release 103 which is followed by fast neural effects 104 after about 0.5 to 5 seconds. Such fast neural effects can include heart rate increase, breathing rate increase, blood pressure rise, blood glucose increase, pupil dilation, slowing down of the digestive system, sweating (via acetylcholine), and the like. The HPA pathway 102 on the other hand leads to cortisol release 105 which causes slow hormonal effects 106, e.g. being most pronounced after 20-30 min, such as increased blood pressure, improved emotional memory, increased vigilance, increased glucose production from glycogen in the liver, and the like. It has been found that fast neural effects can be identified as stimulus responses corresponding to a neural stress response by determining them from a psychophysiological signal trace indicative of such one or more (measured) stimulus responses. In the following non limiting example, the psychophysiological signal trace is a skin conductance signal trace indicative of skin conductance of the user over time and the stimulus responses are skin conductance responses. For further details reference is made to the background information provided in WO 2013/076615.

Figure 2:
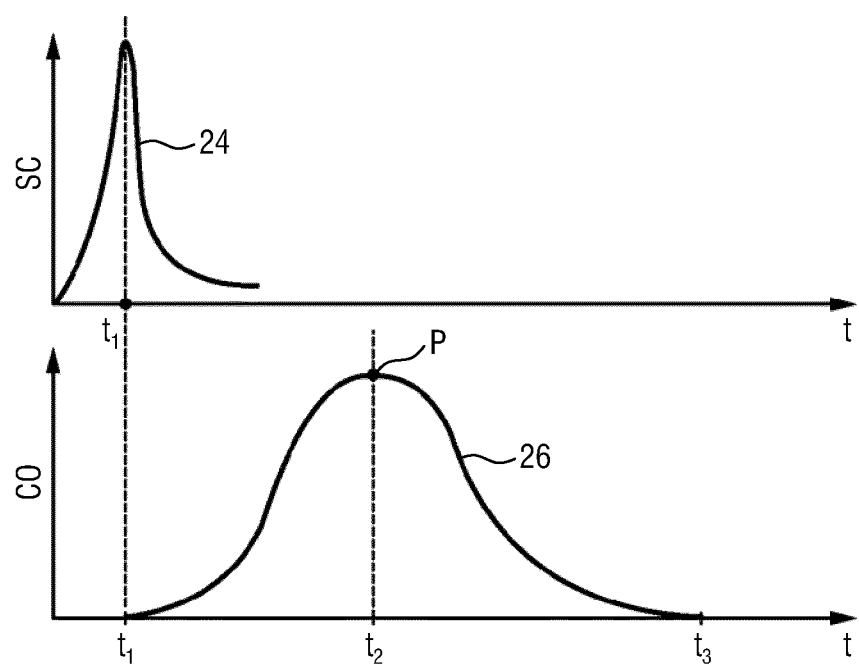
FIG. 2 shows diagrams of an exemplary stimulus response and a corresponding cortisol time response.

FIG. 2 shows diagrams of an exemplary stimulus response 24 (here skin conductance response SC) of a skin conductance trace (top diagram of FIG. 2) and a corresponding cortisol time response 26 (bottom diagram of FIG. 2). As can be seen in FIG. 2, the stimulus response 24 is determined at a specific start point of time t1, and the corresponding cortisol time response 26 has its start point at the specific start point of time t1 and last to its end point at a predetermined time t3 in the future. More specifically, the cortisol time response 26 rises to its peak point P, which is at a predetermined peak point time t2, with a predefined rise coefficient $c_r$ and falls to its end point, which is at a predefined time t3, with a predefined decay coefficient $c_d$. It has been found that such a cortisol time response 26 (or response curve) can be estimated or modeled using the equation:

$$CO(t) = \frac{g \times \exp\left(-\frac{t}{c_d}\right)}{\left(1+\left(\frac{t}{c_r}\right)^{-2}\right)^2}, \quad (1)$$

where CO(t) is the cortisol time response, g is a gain, $c_r$ is the rise coefficient and $c_d$ is the decay coefficient. In particular, time t can be measured in minutes. The gain g corresponds to the height of the peak point P. Thus, the cortisol time response 26 can be modeled with the function with the three descriptors: gain g, rise coefficient $c_r$ and decay coefficient $c_d$. In this way, an estimation of the cortisol response, which closely resembles a salivary cortisol response of the user in reality, can be provided.

The stimulus response (or stress response) and the corresponding cortisol response clearly differs between males and females. Thus, the estimated cortisol time response 26 can depend on an input information which is input into the system 100, for example input to the processing unit 10 and which indicates the sex of the user. The information can, for example, be input by means of a user interface or it can be hard-coded in the system. By taking the sex of the user into account, a more accurate estimation of the cortisol level and thus of the estimated (future) emotional state of the user can be given. For example, the predefined end point of time t3 can depend on the sex of the user. In particular, the predefined end point of time t3 can be about 90 min from the specific start point of time t1 if the input information indicates a female, and about 150 min if the input information indicates a male. Alternatively, the same end point t3 can be used for both sexes, for example t3 can be 180 min for both sexes. Since the down curve is an asymptote, these values are chosen such that the cortisol response has effectively died out (but not exactly). Thus, at the end point of time t3 the cortisol level of the cortisol time response is zero or comes close to zero.

Table I shows a modeling result for the three salivary cortisol response coefficients to a psychosocial stimulus (or stressor) for males and females according to equation (1) above. Exemplary values are provided in table I. In this example, the rise time constant $c_r$ can be almost equal for both sexes, whereas the decay time constant $c_d$ differs significantly. The gain parameter g can be about 1.5 times larger for females than for males.

TABLE I

| Coefficient | male | female |
|---|---|---|
| $c_d$ | 22 | 15 |
| $c_r$ | 25 | 28 |
| g | 124 | 170 |

The estimated cortisol time response (cortisol levels over time) can be additional to a cortisol base level of a real cortisol trace. In a day trace of cortisol there can always be a base level dependent on the time of the day. The cortisol response curve may have a baseline cortisol value of e.g. 4.2 nmol/l. For example, in the morning it is high to wake a person up, and it lowers down to a low value in the evening to facilitate sleep. These effects of the cortisol base level are not necessarily taken into account by the system but can be optionally. The cortisol time response (curve) disclosed herein can be seen as a cortisol level amount additional to the cortisol base level. This additional amount is vanished after a specific time period (e.g. about 150 min). Thus, cortisol level of the estimated cortisol time response is not an estimated value of a real (absolute value) cortisol level.

The cumulated (salivary) cortisol responses which overlap in time yield the estimated cortisol level trace as determined based on the stimulus responses. Since the estimated cortisol level trace is coupled to the stimuli (or stress/arousal peaks) in the psychophysiological signal trace, here the skin conductance trace, the temporal effects of the occurrence of a stimulus (or stressor) and the skin conductance trace becomes visible in the estimated cortisol level trace. Subsequent stimuli (or stressors) clearly cause overlapping cortisol responses.

Thus, the estimated cortisol level trace 28 can be determined by cumulating multiple estimated cortisol time responses 26, wherein each estimated cortisol time response 26 is based on one stimulus response 24. An estimated cortisol level trace 28 comprising several cortisol time responses 26 each corresponding to a stimulus response 24 can be determined by deploying a convolution of a template cortisol response curve, as e.g. given by equation (1) and shown in FIG. 2, lower graph, with the (heights of) the skin respective conductance peaks. In this way a quantification of the cumulative effect of subsequent stimuli (or stressors) in a specific time frame, (e.g. a time frame or several hours) can be provided. Based on these cumulated cortisol responses the emotional state such as a level of mental balance (or imbalance) can be estimated. An advantageous mental state is between over stimulation and under stimulation.

Figure 3:
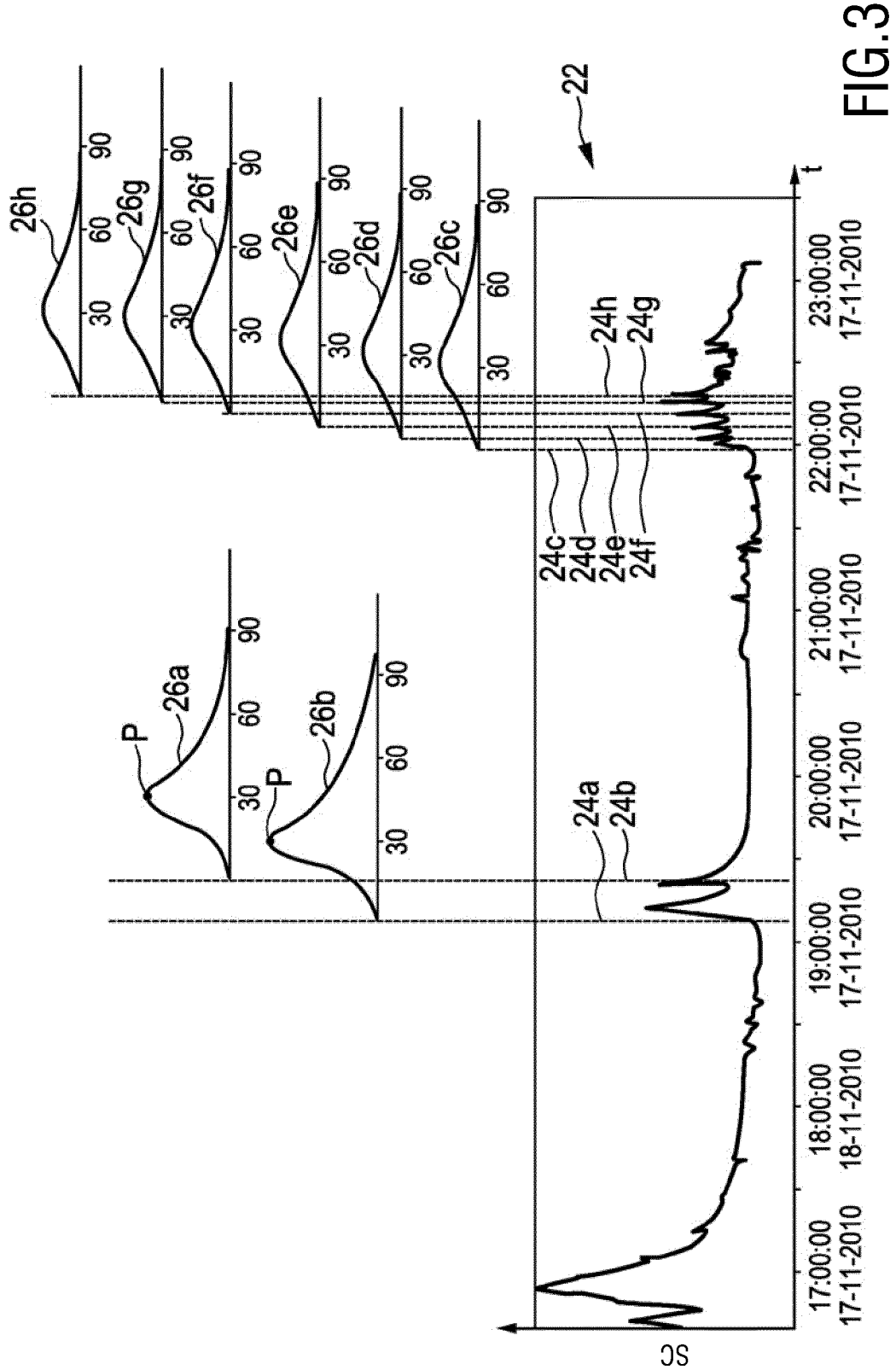
FIG. 3 shows diagrams of an exemplary skin conductance trace having multiple stimuli and the corresponding cortisol time responses.
Figure 6:
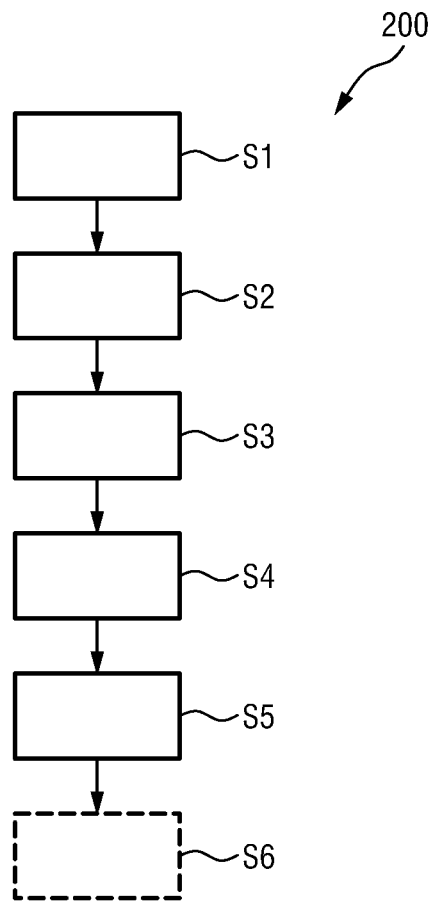
FIG. 6 shows a schematic diagram of a method for determining an emotional state of the user based on emotion-induced cortisol estimation.

FIG. 3 shows an exemplary skin conductance trace 22 having multiple stimuli 24a-h and the corresponding cortisol time responses 26a-h. In particular FIG. 6 shows the skin conductance trace 22 of a female. The skin conductance trace 22 has multiple stimuli 24a-h (or stress/arousal peaks). Coupled to each stimulus response 24a-h is a corresponding or respective salivary cortisol response curve 26a-h. As can be seen in FIG. 6, the predefined peak point of time (t2 in FIG. 2) of the peak point P is about 30 minutes after the start point of time.

The estimated cortisol level trace 28 is then determined by cumulating the multiple estimated cortisol time responses which overlap in time (for example on the one hand cortisol responses 26a and 26b in FIG. 6, and on the other hand cortisol responses 26c-h). The emotional state can therefore be determined or estimated based on the cumulative effect of subsequent stimuli (or stressors), e.g. on the mood/stress state of a person, by assuming that it is related to the cumulative salivary cortisol, which is linked to the intracellular cortisol.

Figure 4:
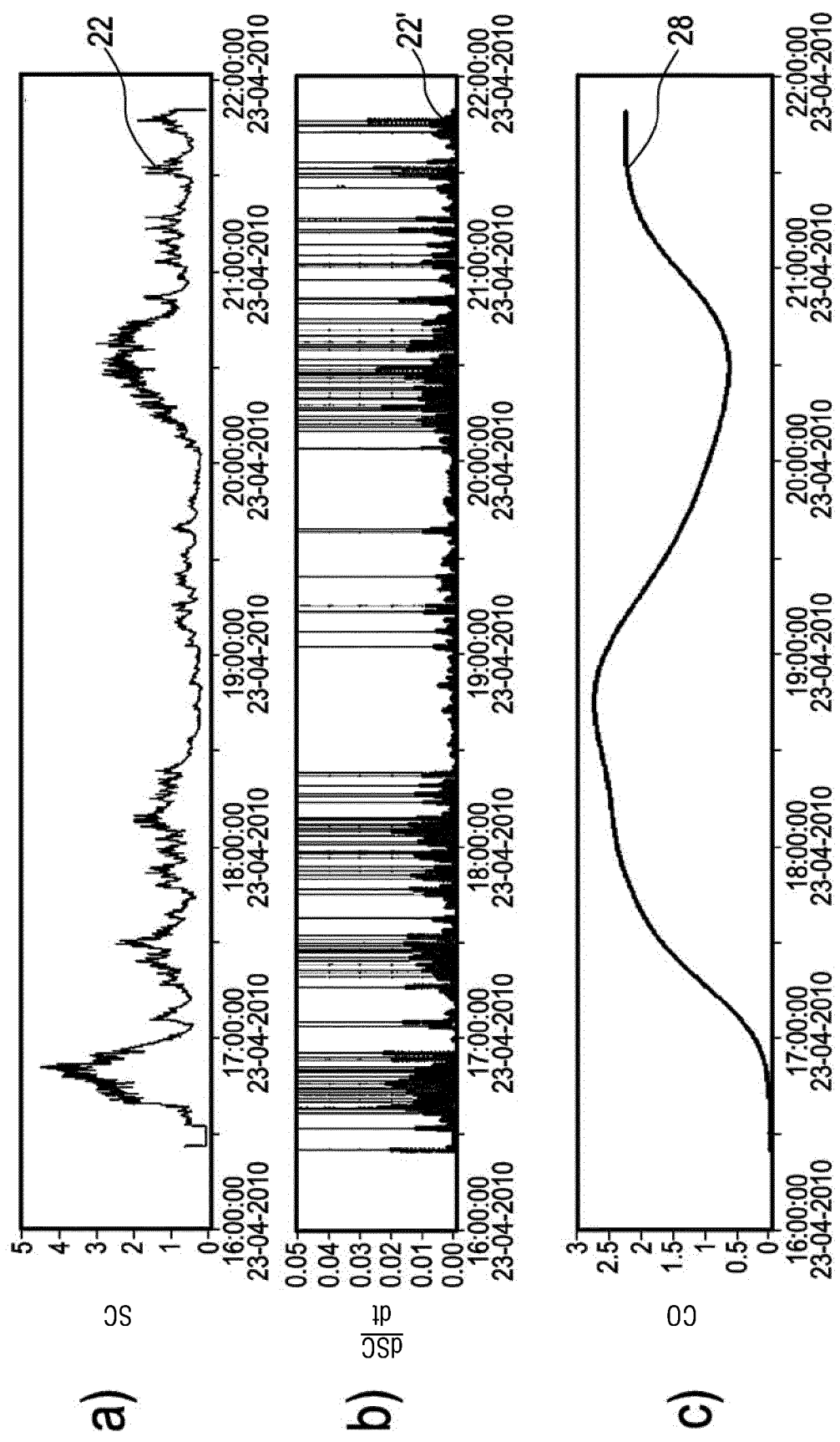
FIG. 4 shows a first example of a) a skin conductance trace, b) the first derivative of the skin conductance trace, and c) an estimated salivary cortisol level trace.

FIG. 4 shows a first example of a skin conductance trace 22 (FIG. 4a), the first derivative 22' of the skin conductance trace (FIG. 4b), and an estimated salivary cortisol level trace 28 (FIG. 4c). In particular, FIG. 4a shows a smoothed skin conductance, FIG. 4c) shows the first derivative d(SC)/dt of the skin conductance and the corresponding peaks (indicated as fine vertical lines), and FIG. 4c) shows the estimated cumulative cortisol.

Figure 5:
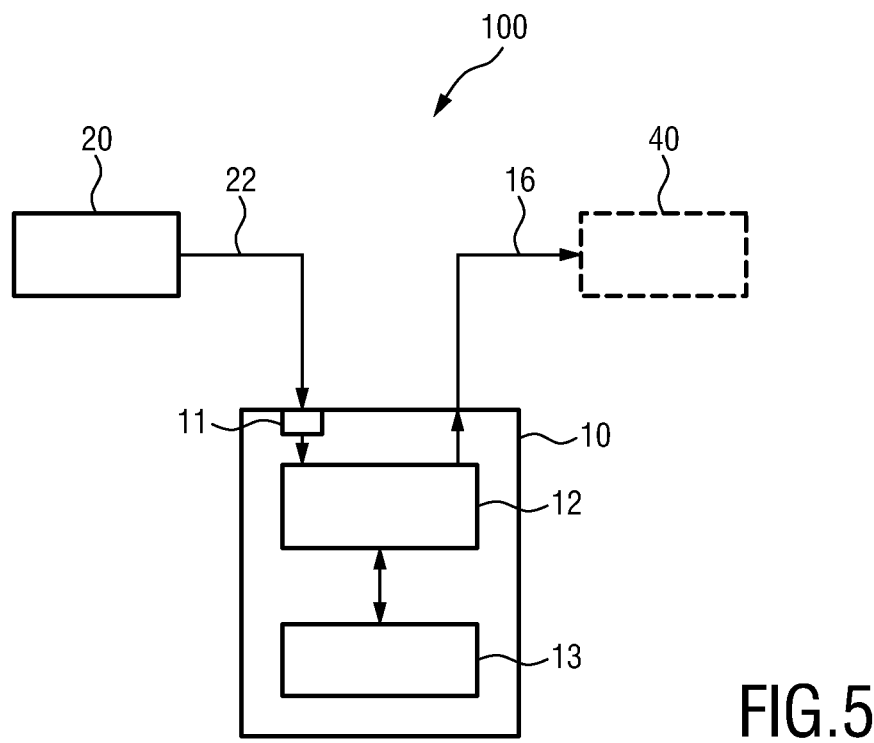
FIG. 5 shows a schematic diagram of an embodiment of a system for determining an emotional state of the user based on emotion-induced cortisol estimation.

FIG. 5 shows a schematic diagram of exemplary embodiment of a system 100 for determining an emotional state of a user based on emotion-induced cortisol estimation. The system 100 comprises a sensor 20 for measuring a psychophysiological signal such as the skin conductance of the user. The psychophysiological signal measured by the sensor 20 over time forms a psychophysiological signal trace 22. The system 100 further comprises a device 10 for determining an emotional state of the user based on emotion-induced cortisol estimation. The device 10 comprises an interface 11 for obtaining the psychophysiological signal trace 22 (indicative of one or more measured stimulus responses 24 corresponding to a neural stress response); and a processing unit 12 for processing the psychophysiological signal trace 22. The processing unit 12 can be any type of suitable processing unit or processor, such as for example a microprocessor/microcontroller, or embedded microcontroller but not limited thereto that is adapted accordingly. Optionally, the processing unit 12 may include multiple microprocessors that are configured to either independently execute the steps of the method described herein or are configured to perform steps or subroutines of the method described herein such that the multiple processors cooperate to achieve the functionality, i.e. processing the psychophysiological signal trace, described herein. Further, where the system 100/ device 10 is implemented in a cloud computing system, the various hardware components may belong to separate physical systems. It will be understood that the sensor 20 and the device 10 can be part of the same device (e.g. wearable device or wristband) or can be in separate devices.

The processing unit 12 is configured to determine (or compute) one or more stimulus responses 24 in the psychophysiological signal trace 22 (for example by evaluating a first order derivative of the psychophysiological signal trace or by other methods of feature detection), to determine a first contribution to an estimated future cortisol level trace based on the one or more determined stimulus responses in the psychophysiological signal trace; to determine a second contribution to the estimated future cortisol level trace based on or more anticipated future stimulus responses; and to determine an estimated future emotional state of the user based on said first and said second contribution to the estimated future cortisol level trace.

Optionally, as indicated by the dashed lines in FIG. 5, the system can comprise an output unit 40 for outputting or rendering the estimated future emotional state 16 to a user. It will be understood that the output unit 40 and the device 10 can be part of the same device (e.g. wearable device or wristband) or can be in two separated devices. For example, the output unit 40 of the system 100 can be implemented by means of a smartphone or other information processing entity at the same or a remote location. Correspondingly, the processing unit 12 can also be implemented by means of a smartphone that is adapted to perform the afore-mentioned functionality for example by running a corresponding app or another suitable computing device running the corresponding software.

The system 100 can further comprise a memory 13 for storing an estimated future cortisol level trace. The estimated future cortisol level trace can be determined by cumulating the first contribution and the second contribution to the estimated future cortisol level trace. The first contribution to the estimated future cortisol level trace can be determined by cumulating multiple estimated cortisol time responses, wherein each estimated cortisol time response 26 is based on one of the determined stimulus responses 24 in the (measured past) psychophysiological signal trace. Correspondingly, the second contribution to the estimated future cortisol level trace can be determined by cumulating multiple estimated cortisol time responses, wherein each cortisol time response is based on one anticipated future stimulus responses.

Hence, the estimated future cortisol level trace can be established by adding the corresponding estimated cortisol time responses to the estimated future cortisol level trace for each of the determined stimulus responses and the anticipated future stimulus responses. Thus, multiple estimated cortisol time responses 26 can be cumulated in order to estimate the future cortisol level trace which may then be stored in the memory 13. The memory 13 can be part of the device 10 or can be an external memory. More specifically, for each point of time, the cortisol levels of different cortisol time responses for that point of time may be added or cumulated. The memory can be any suitable memory such as for example a memory register or RAM (random access memory). It will be understood that the memory 13 and the processing unit 12 can be part of the same device (e.g. wearable device or wristband) or can be in two separate devices.

FIG. 6 shows a schematic diagram of a method 200 for determining an emotional state of the user based on emotion-induced cortisol estimation. The method 200 comprises the first step S1 of obtaining (i.e. receiving or retrieving) a psychophysiological signal trace (data) indicative of one or more measured stimulus responses corresponding to a neural stress response. For example, the psychophysiological signal trace can be obtained directly as output data from a sensor (or preprocessing unit) or can be retrieved from storage means, for example, a memory or a hospital information system (HIS) or electronic health record (EHR) of the user.

In the next step S2 one or more stimulus responses in the psychophysiological signal trace are determined (e.g. by evaluating the first order derivative). In step S3 a first contribution to an estimated future cortisol level trace is determined based on the one or more determined stimulus responses in the psychophysiological signal trace as determined in the preceding step S2.

In step S4 a second contribution to the estimated future cortisol level trace is determined based on the one or more anticipated future stimulus responses and in step S5 the estimated future emotional state of the user is determined based on said first and said second contribution to the estimated future cortisol level trace as determined in the preceding steps S3 and S4. These steps can also be performed by a processing unit or a computer program comprising program code means for causing a computer to carry out these steps.

Optionally, as indicated by the dashed lines, the method can further comprise the step S6 of outputting the estimated future emotional state of the user, for example to the user himself or medical personnel.

Figure 7:
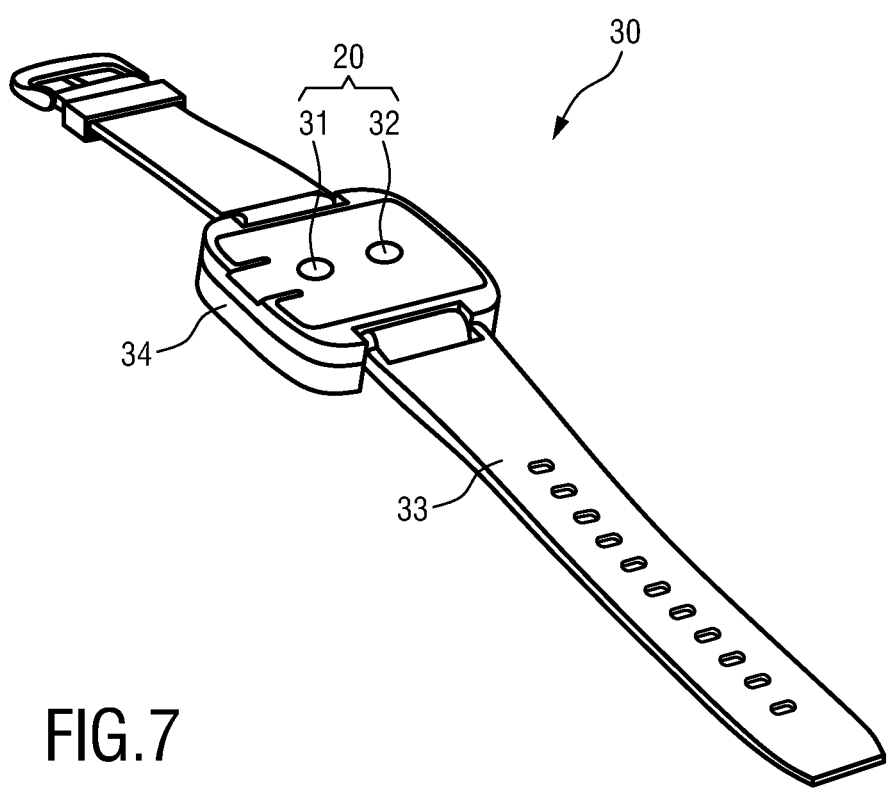
FIG. 7 shows a schematic diagram of a wearable device.

FIG. 7 shows an embodiment of a wearable device 30 wearable by user according to an embodiment. In this embodiment, the wearable device is in form of a smart watch. The smart watch comprises a wristband 33 and a casing 34. The wristband 33 can loop around the wrist of the user. It will be understood that a wearable device could also be worn around another suitable part of the body such as the ankle foot or hand or may be adapted for attachment to other parts of the body.

The wearable device 30 can comprise the proposed system 100 for determining an emotional state of the user based on emotion-induced cortisol estimation. In this way a corresponding system 100 can be provided in an unobtrusive and wearable format. Alternatively, the wearable device 30 may only comprise the skin conductance sensor 20 and the device 10 of the system 100 may be located at the remote location or implemented in a remote device (e.g. a remote computer, smartphone or patient monitor).

The wearable device 30 comprises the skin conductance sensor 20. The skin conductance sensor can comprise a first and a second skin conductance electrode 31, 32 in combination with a skin conductance measuring unit (not shown). In the embodiment of FIG. 7, two skin conductance electrodes 31, 32 are integrated into the casing of the wearable device, however is also possible to integrate them for example into the wristband 33. The skin conductance electrodes 31, 32 can be arranged so as to contact the upper side of the wrist when the wearable device 30 is worn by the user. An exemplary implementation of a wearable device comprising a skin conductance sensor is the Philip's discrete tension indicator DTI-4.

The skin conductance measuring unit is adapted to measure the skin conductance of the user 2 between the skin conductance electrodes 31, 32. In particular, the skin conductance measuring unit or sensor can comprise a voltage generator for applying a voltage between the at least two skin conductance electrodes, a sensing unit for sensing a current between the at least two electrodes, and/or a calculating unit for calculating the skin conductance based on the sensed current. The measured skin conductance over time forms, in this embodiment, the psychophysiological signal trace (or data). The psychophysiological signal trace (or data) can for example be stored in a memory of the wearable device 30, or can be (wirelessly) transmitted to an external unit using a (wireless) transmitter. The skin conductance measuring unit and/or the device 10 (FIG. 5) can be integrated into the casing 34 of the wearable device 30. The wearable device 30 can further comprise a transmitter for wirelessly transmitting data over a wireless communication link, such as the output data or the estimated emotional state 16 of the user. However, it will be understood that the device 10 or processing unit 12 can also be a separate part or device and that the wearable device 30 then transmits the psychophysiological data to the separate part or device via the (wireless) transmitter.

Advantageously, the system can also comprise an output unit for outputting the emotional state of the user 1. The output unit 40 can be a separate device or can be integrated into, for example, the wearable device 30 comprising the sensor 20 in form of a smart watch. Furthermore, an external output unit 40 for example a smartphone running a corresponding app, can be used and coupled to the device 10 or wearable device 30.

Figure 8:
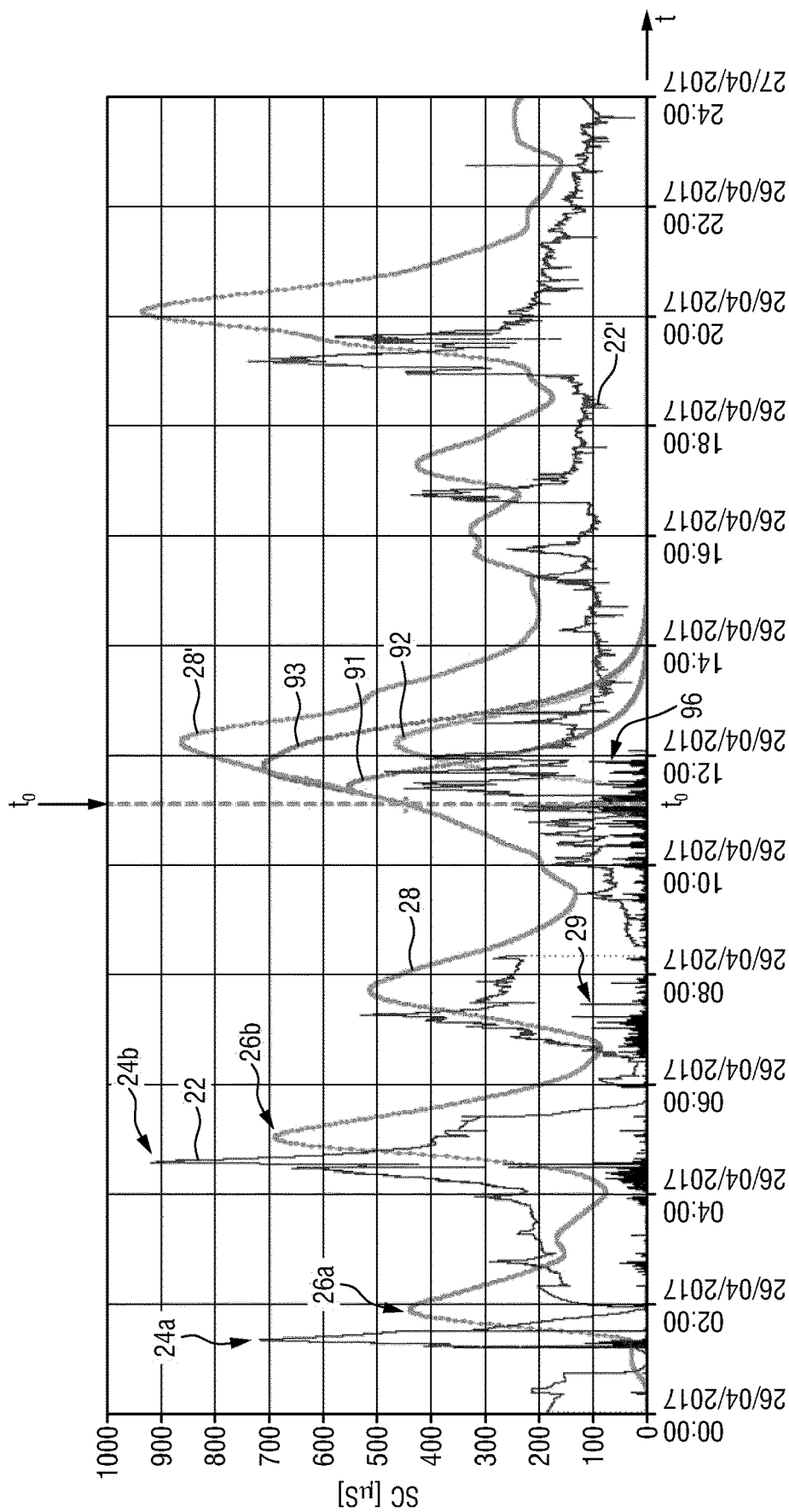
FIG. 8 shows a diagram of a psychophysiological signal trace, determined past stimulus responses prior to time $t_0$ and estimated future stimulus responses after time $t_0$, an reference cortisol level trace, a first contribution to an estimated future cortisol level trace, a second contribution to the estimated future cortisol level trace, and the estimated future cortisol level trace based on said first and said second contribution.

FIG. 8 shows an exemplary psychophysiological signal trace 22, in the present non-limiting embodiment in form of a skin conductance trace measured by a skin conductance sensor 20. The horizontal axis denotes the time t of a period of several hours, here an entire day from midnight to midnight. The vertical axis denotes the measured skin conductance values SC of the skin conductance trace also called galvanic skin response (GSR) or electrodermal activity (EDA), measured in μS. Each point of the skin conductance trace indicates the skin conductance values sensed by the skin conductance sensor at that specific point in time t. Skin conductance (or GSR or EDA), is a measure of the electrical conductance of the skin, which varies with its moisture level, thus the sweat gland activity.

Emotional events or stimuli typically show as peaks with a steeper rising slope and a gentler down slope. In FIG. 8 each peak corresponds to a response of the sympathetic nervous system to an emotionally arousing event (communicated via the vagal nerve to the sweat glands of the skin). This peak is also referred to as a skin conductance response (or more generally stimulus response). Emotionally arousing events or stimuli can be viewed as psychological stress, in contrast to physical exercise, which can be viewed as physical stress. Thus, an emotional event or stimulus causes (with a short latency, as illustrated in FIG. 2) a stimulus response in the skin conductance which can be measured. Exemplary, particularly pronounced peaks of the skin conductance are indicated by arrows 24a and 24b in FIG. 8. As described above, the stress response further comprises a hormonal effect on a slower time scale e.g. with a latency of 20-30 min. The responses to the peaks 24a and 24b in the estimated cortisol level trace are indicated by reference numerals 26a and 26b. The stimulus responses in the psychophysiological signal trace 22 can be determined by taking the first order derivative to identify skin conductance peaks as exemplarily described in WO 2013/076615 A1.

In FIG. 8, the stimulus responses that occur within a predetermined time interval, for example within one minute, are indicated by a trace of bar graphs 29. For example, the bar graphs as shown in FIG. 8 can indicate the sum of rising edge amplitudes per minute as a measure of the stimulus response(s). In the given example, the bar graphs thereby represent the skin conductance response (SCR) frequency and the skin conductance level (SCL). The sum of rising edges per time interval (e.g. per minute) can be derived from the skin conductance using the first derivative of the skin conductance. A negative to positive zero crossing of the first derivative of the time dependence of the skin conductance may signal the onset of a rising edge. The next zero crossing (positive to negative) of the first derivative of the time dependence of the skin conductance may signal the end of the rising edge. The skin conductance value at the end may be divided by the skin conductance value at the onset to generate the rising edge height. This is a dimensionless value. Optionally, a duration of the rising edge may be evaluated. For example, all rising edge heights for which the criterion is met that the duration of the rising edge exceeds a predetermined duration of for example 1 second in a minute can be summed to generate the sum of (valid) rising edge heights per minute. It should be noted that a rising edge may continue into the next minute. Optionally, if such a rising edge meets the duration criterion, its contribution until the end of the minute may be attributed to that minute. A remainder contribution may be attributed to the next minute and so forth. The sums of rising edges per minute are the vertical bars in FIGS. 8 to 10. In an embodiment, the sum of rising edge amplitudes may be determined as the stimulus responses in the psychophysiological signal trace. Based thereon, the estimated cortisol level trace can be determined by deploying a convolution of the respective skin conductance responses with a template cortisol time response curve (cf. e.g. equation (1) above), in the given example for each minute a convolution of the bar height as given by trace 29 with the template cortisol time response in order to obtain the estimated cortisol level trace 28.

FIG. 8 shows a psychophysiological signal trace 22 for an entire day, here an actual experimental skin conductance trace. In order to evaluate the estimation of the estimated future cortisol level trace of a user as described herein, it is assumed that the psychophysiological signal trace 22, i.e. the actually measured data is only available up to a certain point in time indicated by time $t_0$, e.g., at 11:04 h. Hence, in FIG. 8, the (assumed) current point in time is indicated by a vertical dashed line at time $t_0$. The time before $t_0$ refers to the past, the time after $t_0$ refers to the future. For the purpose of evaluating the solution as described herein, the portion of the psychophysiological signal trace after time $t_0$, denoted by 22', is assumed to lie in the future and is not available for the estimation of the future cortisol level trace (cf. reference numerals 91, 92, 93).

For comparison only, the estimated cortisol level trace 28' following time $t_0$ is calculated by also taking the stimulus responses in the psychophysiological signal trace 22' into consideration. Herein, the estimated cortisol level trace 28' serves as a reference cortisol level trace.

Figure 9:
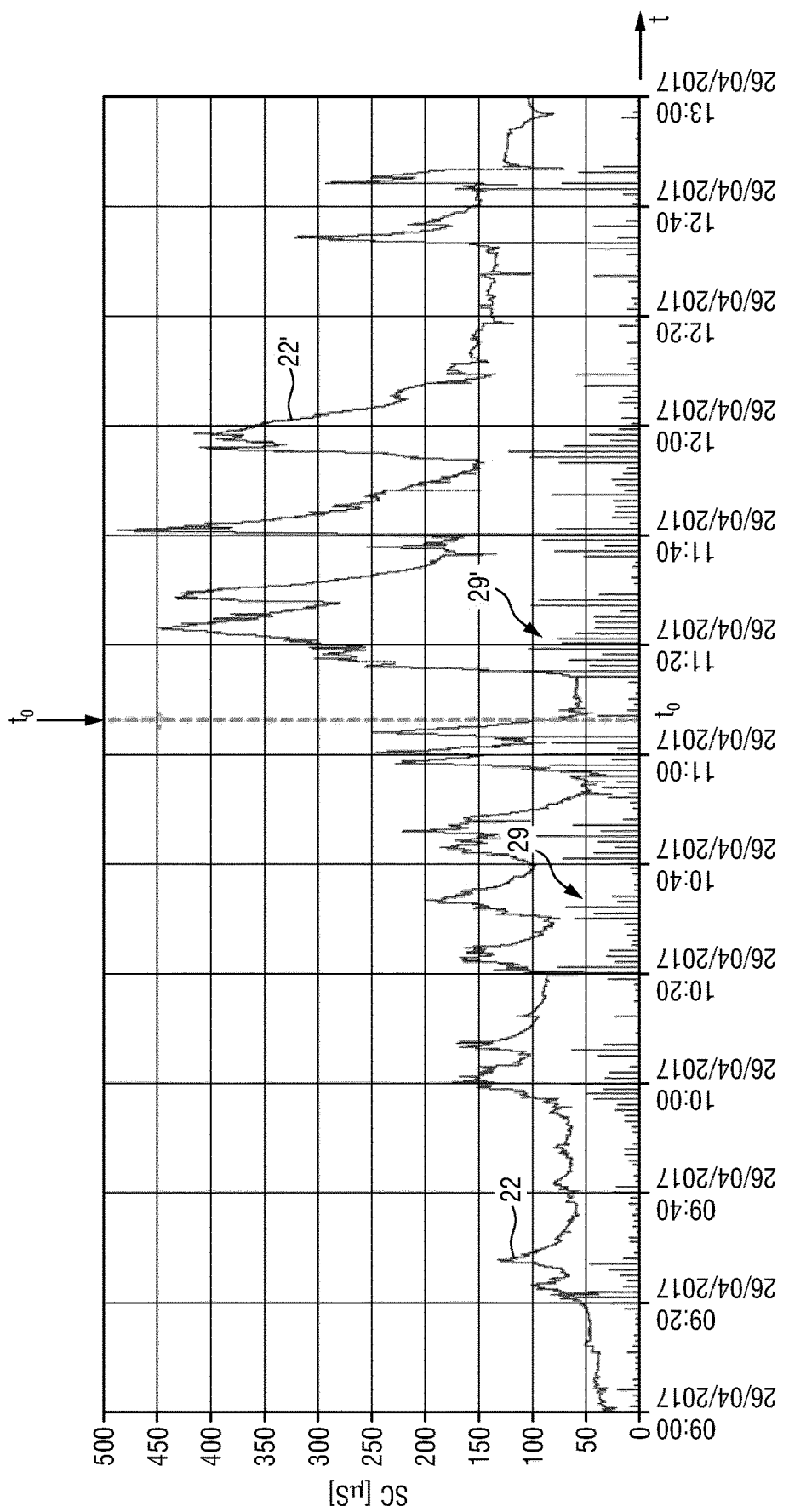
FIG. 9 shows a diagram of the psychophysiological signal trace of FIG. 8 as well as detected stimulus responses for the entire signal trace.

FIG. 9 shows a zoomed-in portion of the psychophysiological signal trace 22 and 22' of FIG. 8, as well as determined stimulus responses for the entire signal trace including past stimulus responses as indicated by the bar graph 29 before time $t_0$ and stimulus responses as indicated by the bar graph 29' after time $t_0$. Obviously, at time $t_0$ the future stimulus responses 29' are not available yet at $t_0$.

Figure 10:
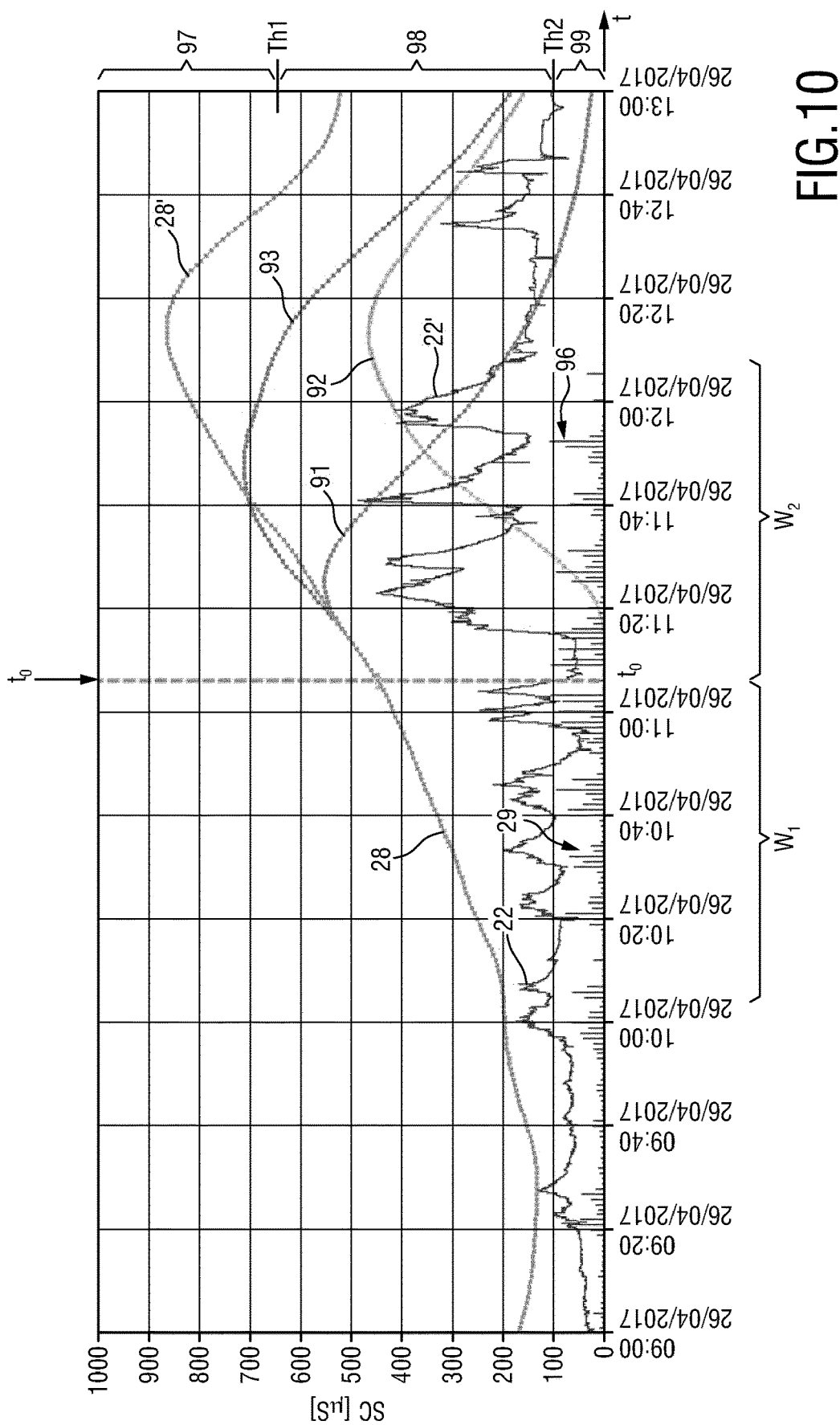
FIG. 10 shows a zoomed-in portion of the diagram of FIG. 8.

Turning now to FIG. 10, this diagram shows a zoomed-in portion of the diagram of FIG. 8 between 9:00 h and 13:00 h. For the time prior to the current point in time $t_0$, the psychophysiological signal trace 22 is available such that the stimulus responses 29 in the psychophysiological signal trace can be determined and represented herein as a sum of rising edge amplitudes indicative of the cumulated rising edges in the skin conductance signal 22 per minute. For each of these stimulus responses, a corresponding (delayed) cortisol response can be calculated by calculating a convolution of the stimulus response with an estimated cortisol time response 26 as also illustrated with respect to FIG. 3. The curve denoted by reference numeral 91 represents a first contribution to an estimated future cortisol level trace 93 based on the one or more determined stimulus responses 29 in the (measured past) psychophysiological signal trace, i.e. only taking into account actually measured psychophysiological data before time $t_0$ (i.e. the way of determining the cortisol level trace as described in WO 2013/076615 A1). Hence, this curve represents the case that not a single future stimulus response is taken into account after time $t_0$, as if the user would not be exposed to any future stressors at all abruptly.

The solution according to the present disclosure further takes a second contribution 92 to the estimated cortisol level trace 93 into consideration based on one or more anticipated future stimulus responses 96. In the given example, the anticipated future stimulus responses 96 in a second time window w2 immediately after time $t_0$ (here from 11:04 to 12:04) correspond to the determined stimulus responses 29 in a first time window w1 immediately preceding time $t_0$ (here from 10:04 to 11:04). Different lengths of the respective time windows can be chosen. The determined stimulus responses 29 are thus determined based on the actually measured past psychophysiological signal trace 22 preceding the current point in time $t_0$. In the given embodiment, the determined stimulus responses 29 preceding the time $t_0$ are essentially mirrored after the time $t_0$ in order to obtain the anticipated stimulus responses 96. For each of these anticipated stimulus responses 96, the contribution to the cortisol level trace can again be determined by calculating a convolution with the cortisol time response 26, as e.g. described with reference to FIG. 3. By calculating the convolution, both the timing as well as the strength of the respective stimulus responses are taken into consideration correctly.

Hence, in the example shown in FIG. 8 and FIG. 10, the first contribution 91 to the estimated future cortisol level trace 93 is determined for an upcoming second predetermined time window w2 of 60 min after time $t_0$ based on the determined (measured past) stimulus responses 29 in the psychophysiological signal trace 22 in a past first predetermined time window of 60 min preceding the time $t_0$. The second contribution 92 to the estimated future cortisol level trace 93 in this upcoming second predetermined time window w2 is based on one or more anticipated future stimulus responses 96, which are expected to occur in said second predetermined time window. In the given example, the anticipated future stimulus responses correspond to the past (measured) stimulus responses in the first predetermined time window wherein said stimulus responses are reversed in order with respect to the stimulus responses in the first time window.

Referring now to the comparison with the estimated cortisol level trace 28' (i.e. the reference cortisol level trace 28' under the assumption that that the psychophysiological signal trace 22' after time t0 is available): The first contribution 91 already provides an accurate approximation over the first 10-15 min of the cortisol level trace 28'. This is reasonable because the cortisol response to a stimulus response after time $t_0$ has a latency and only provides a significant contribution thereafter (as can be seen from the slowly rising curve 92 that is indicative of contributions after time $t_0$). However, thereafter the first contribution 91 underestimates the future cortisol level.

The approach described herein provides a further improvement of the estimated future cortisol level trace 93 and thus enables a more accurate and more robust estimation of the future emotional state of the user by also taking the second contribution 92 to the estimated future cortisol level trace based on the anticipated future stimulus responses 96 into account. The estimated future cortisol level trace 93 comprises the sum of the first contribution 91 and the second contribution 92. As can be seen in FIG. 10 from about 15 min onwards, the estimated future cortisol level trace 93 more closely matches the reference cortisol level trace 28'.

It shall be understood that the anticipated future stimulus responses indicative of an estimation of an expected frequency and severity of stressors between the current point in time $t_0$ and the moment for which the cortisol prediction is needed can be done in several ways based on several assumptions. As explained above, one possibility is to assume that the user keeps doing what he has been doing in the past period. In that case also the psychophysiological signal trace expected for the upcoming time will be very similar, for example with respect to the skin conductance response (SCR) frequency and skin conductance level (SCL) and the corresponding sum of rising edges of SCRs and SCL changes per time segment, to the psychophysiological signal trace that was most recently measured. Hence, at least segments of the psychophysiological signal trace preceding the current point in time can be taken as a basis for the estimation of the expected frequency and severity of stressors between now and the predicted moment. For example, if the moment for which a cortisol prediction is needed lies 28 min into the future, the skin conductance responds frequency and skin conductance level and sum of rising edges of SCRs and SCL changes of the time segment of the last 28 min can be taken into account as an estimate of the stressor the user will encounter in that period. For example, in determining the estimated future cortisol level trace the stimulus responses in the past 28 min can be used twice: once for the time it was actually measured (in the past) and once as an estimate for the time that lies in the future, i.e. the time window following $t_0$.

Advantageously, as also shown in FIG. 10, the psychophysiological trace or the stimulus responses determined based thereon can be used in reversed form using the most recent stimulus responses in the near future and the less recent measurement values or stimulus responses in the further future. By mirroring the input this way, the near future estimates will become more reliable than further future estimates, which can be advantageous for coaching a user. In addition or in the alternative, since the most recent time is usually most reliable, it is also possible to consider the most recent psychophysiological signal trace and/or stimulus responses determined based thereon several times. Optionally, an average future stimulus response can be anticipated per time segment, for example an average expected stimulus response contribution per minute, for example by taking an average of one or more determined stimulus responses in a predetermined past time window. Optionally, one or more anticipated future stimulus responses can be determined based on the assumption that the user will be doing what he did during that same period on a previous day, for instance yesterday, or last week on the same day of the week, or on a similar working or leisure day. Optionally, it is also possible to use the weighted average for determining the anticipated future stimulus responses based on each of the above options and then take their weighted average as an estimation of the contribution of anticipated future stimulus responses that will provide additional contributions to the estimated future cortisol level trace.

Referring again to FIG. 10, based on the estimated future cortisol level trace 93 including said first contribution 91 and said second contribution 92, an estimated future emotional state of the user can be determined. For example, as illustrated in FIG. 9, the user can be classified into an overstimulated state 97 if the estimated future cortisol level trace 93 exceeds a first threshold Th1; classified into a balanced (healthy) state if the estimated future cortisol level trace 93 is in the range between the first threshold Th1 and a second threshold Th2, i.e., in the range denoted by 98; and may be classified as being in an understimulated state 99 if the cortisol level trace falls below the second threshold Th2. Hence, it is possible of warning the user of upcoming periods of too high cortisol levels, in which his cognitive performance might be lower than optimal.

Furthermore, the system can be adapted to provide coaching based on predictions based on different assumptions of future exposition to stressors, i.e., based on different anticipated stimulus responses (in terms of frequency and/or intensity). For example, the trace indicated by reference numeral 93 can be seen as a prediction under the assumption that the user keeps doing what he has been doing lately/normally. The prediction can indicate when the user will end to enter a cognitive less optimal state, and how long he is expected to stay there, in case he keeps doing what he has been doing recently. On the other hand, the trace indicated by reference numeral 91 can be seen as a prediction under the assumption that the user abruptly stops exposition to any further stressors after time t, i.e. that the user avoids all stress from now on.

Moreover, in an embodiment the user can be provided with coaching in the different direction, for example, if the user is approaching and understimulated state 99, advice can be given to engage in a more challenging activity to raise the estimated future cortisol level trace into the healthy zone 98.

Considering different cortisol predictions may thus allow the user to get an estimate of expected beneficial effects of e.g. indeed taking a (non-stressing) break or engaging in a more challenging activity in comparison to continuing with the current activity. For implementing this option, the processing unit can be configured to determine a first and a second estimated future emotional state of the user by (a) determining a first second contribution to the estimated future cortisol level trace based on one or more first anticipated future stimulus responses; and determining a first estimated future emotional state of the user based on said first and said first second contribution to the estimated future cortisol level trace. For example, this can be the case that the user keeps doing what he has been doing. Furthermore, the second estimated future emotional state can be determined by determining a second second contribution to the estimated future cortisol level trace based on zero or more second anticipated future stimulus responses, and determining a second estimated future emotional state of the user based on said first contribution to the estimated future cortisol level trace and said second second contribution for the estimated future cortisol level trace.

In conclusion, the solutions proposed herein can provide an improved estimation of a future emotional state of the user based on said first and said second contribution to the estimated future cortisol level trace. In particular, the future estimation accuracy is further improved and also a time interval for which a prediction can be reliably made can be extended.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device wearable by or attachable to a user during an activity by the user, the device for determining and communicating an estimated future emotional state of the user based on an emotion-induced cortisol estimation during the activity by the user, the device comprising:
an interface circuit,
wherein, when the device is worn by or attached to the user during the activity by the user, the interface circuit is configured to obtain a psychophysiological signal trace indicative of one or more measured stimulus responses, and
wherein the one or more measured stimulus responses correspond to a neural stress response;
a processing circuit,
wherein, when the device is worn by or attached to the user during the activity by the user, the processing circuit, during the activity by the user, is configured to:
process the psychophysiological signal trace,
determine the one or more stimulus responses indicated in the psychophysiological signal trace, determine a first contribution to an estimated future cortisol level trace based on the one or more determined stimulus responses indicated in the psychophysiological signal trace, determine a second contribution to the estimated future cortisol level trace based on one or more anticipated future stimulus responses, and determine the estimated future emotional state of the user based on the first contribution to the estimated future cortisol level trace and the second contribution to the estimated future cortisol level trace;

and wherein the device wearable by or attachable to the user is configured to communicate the estimated future emotional state of the user to effect a modification in the activity of the user when the estimated future emotional state of the user indicates an overstimulated state of the user in response to the activity by the user;

where the communication includes advice to the user to cease performing the activity during a period where the estimated future emotional state of the user indicates the overstimulated state;

where the communication includes a warning detailing a duration of the period of the overstimulated state;

where the device includes one or more of: (1) a smartwatch configured to be worn by or attached to the user, or (2) a band into which the device is placed, the band configured to be worn around or attached to a hand, wrist, foot, or ankle of the user.

2. The device as claimed in claim 1, wherein the psychophysiological signal trace is a skin conductance signal trace indicative of a skin conductance of the user over time.

3. The device as claimed in claim 1,
wherein the processing circuit is configured to determine the first contribution to the estimated future cortisol level trace in an upcoming second predetermined time window;
wherein the determination of the first contribution to the estimated future cortisol level trace is based on the one or more determined stimulus responses indicated in the psychophysiological signal trace in a past first predetermined time window;
wherein the processing circuit unit is configured to determine the second contribution to the estimated future cortisol level trace in the upcoming second predetermined time window; and
wherein the determination of the second contribution to the estimated future cortisol level trace is based on the one or more anticipated future stimulus responses,
where the one or more anticipated future stimulus responses are expected to occur in the upcoming second predetermined time window.

4. The device as claimed in claim 3, wherein the anticipated future stimulus responses are determined based on the one or more past stimulus responses in the psychophysiological signal trace in the past first predetermined time window.

5. The device as claimed in claim 4, wherein the one or more stimulus responses in the upcoming second predetermined time window are equal to, or reversed in order with respect to, the one or more stimulus responses in the past first predetermined time window.

6. The device as claimed in claim 1, wherein determining the second contribution to the estimated future cortisol level trace includes:
extrapolating the psychophysiological signal trace to obtain an extrapolated psychophysiological signal trace; and
determining the one or more anticipated future stimulus responses in the extrapolated psychophysiological signal trace.

7. The device as claimed in claim 6, wherein the processing circuit is configured to extrapolate the psychophysiological signal trace such that at least a segment of the extrapolated psychophysiological signal trace corresponds to a segment of the psychophysiological signal trace.

8. The device as claimed in claim 6, wherein the processing circuit is configured to extrapolate the psychophysiological signal trace such that at least a segment of the extrapolated psychophysiological signal trace corresponds to a segment of the psychophysiological signal trace that is reversed in time.

9. The device as claimed in claim 1, wherein the processing circuit is configured to determine the second contribution to the estimated future cortisol level trace based on historic data indicative of the one or more anticipated future stimulus responses.

10. The device as claimed in claim 1,
wherein the processing circuit is configured to determine the estimated future emotional state including a first estimated future emotional state of the user and a second estimated future emotional state of the user;
wherein the determining the second contribution to the estimated future cortisol level trace based on one or more anticipated future stimulus responses includes:
determining an initial second contribution to the estimated future cortisol level trace based on one or more first anticipated future stimulus responses; and
determining an additional second contribution to the estimated future cortisol level trace based on one or more second anticipated future stimulus responses; and
wherein the determining of the first estimated future emotional state of the user and the second estimated future emotional state of the user includes:
determining the first estimated future emotional state of the user based on the first contribution to the estimated future cortisol level trace and the initial second contribution to the estimated future cortisol level trace; and
determining a second estimated future emotional state of the user based on the first contribution to the estimated future cortisol level trace and the additional second contribution to the estimated future cortisol level trace.

11. The device as claimed in claim 10, wherein the additional second contribution to the estimated future cortisol level trace is lower than the initial second contribution to the estimated future cortisol level trace.

12. A system for determining an emotional state of a user based on emotion-induced cortisol estimation, the system comprising:
a sensor, wherein the sensor is configured to measure a psychophysiological signal indicative of one or more measured stimulus responses corresponding to a neural stress response of the user; and
the device as claimed in claim 1.

13. A method for determining and communicating an estimated future emotional state of a user based on emotion-induced cortisol estimation, the method being performed by a device worn by or attached to a user during an activity by the user, the method comprising:
by the device as worn by or attached to the user during the activity of the user,
obtaining a psychophysiological signal trace indicative of one or more measured stimulus responses corresponding to a neural stress response;

determining the one or more stimulus responses indicated in the psychophysiological signal trace;
determining a first contribution to an estimated future cortisol level trace based on the one or more determined stimulus responses indicated in the psychophysiological signal trace;
determining a second contribution to the estimated future cortisol level trace based on one or more anticipated future stimulus responses;
determining the estimated future emotional state of the user based on the first contribution to the estimated future cortisol level trace and the second contribution to the estimated future cortisol level trace;
determining the estimated future emotional state to be an overstimulated state; and
communicating the estimated future emotional state of the user to effect a modification in the activity of the user when the estimated future emotional state of the user indicates the overstimulated state of the user in response to the activity by the user;
where the communication includes advice to the user to cease performing the activity during a period where the estimated future emotional state of the user indicates the overstimulated state;
where the communication includes a warning detailing a duration of the period of the overstimulated state;
where the device includes one or more of: (1) a smartwatch configured to be worn by or attached to the user, or (2) a band into which the device is placed, the band configured to be worn around or attached to a hand, wrist, foot, or ankle of the user.

14. The method as claimed in claim 13, further comprising:
determining the first contribution to the estimated future cortisol level trace in an upcoming second predetermined time window based on the one or more determined stimulus responses indicated in the psychophysiological signal trace in a past first predetermined time window; and
determining the second contribution to the estimated future cortisol level trace in the upcoming second predetermined time window based on one or more anticipated future stimulus responses,
wherein the one or more anticipated future stimulus responses are expected to occur in the upcoming second predetermined time window.

15. The method as claimed in claim 13, wherein the determining the second contribution to the estimated future cortisol level trace includes:

extrapolating the psychophysiological signal trace to obtain an extrapolated psychophysiological signal trace;
determining the one or more anticipated future stimulus responses in the extrapolated psychophysiological signal trace.

16. The method as claimed in claim 15, wherein the extrapolating the psychophysiological signal trace includes extrapolating the psychophysiological signal trace such that at least a segment of the extrapolated psychophysiological signal trace corresponds to a segment of the psychophysiological signal trace that is reversed in time.

17. The method as claimed in claim 13, further comprising determining the second contribution to the estimated future cortisol level trace based on historic data indicative of the one or more anticipated future stimulus responses.

18. The method as claimed in claim 13, further comprising determining the estimated future emotional state including a first estimated future emotional state of the user and a second estimated future emotional state of the user;
wherein the determining the second contribution to the estimated future cortisol level trace based on one or more anticipated future stimulus responses includes:
determining an initial second contribution to the estimated future cortisol level trace based on one or more first anticipated future stimulus responses; and
determining an additional second contribution to the estimated future cortisol level trace based on one or more second anticipated future stimulus responses; and
wherein the determining of the first estimated future emotional state of the user and the second estimated future emotional state of the user includes:
determining the first estimated future emotional state of the user based on the first contribution to the estimated future cortisol level trace and the initial second contribution to the estimated future cortisol level trace; and
determining the second estimated future emotional state of the user based on the first contribution to the estimated future cortisol level trace and the additional second contribution to the estimated future cortisol level trace.

19. A computer program stored on a non-transitory medium, wherein the computer program when executed on a processor performs the method as claimed in claim 13.

* * * * *